(12) United States Patent
Gupta et al.

(10) Patent No.: US 6,225,468 B1
(45) Date of Patent: May 1, 2001

(54) PROCESS FOR MAKING 2-(2,4,-DIHYDROXYPHENYL) OR 2-(2,4-DIALKOXYPHENYL)-4,6-BISARYL-1,3,5-TRIAZINES

(75) Inventors: Ram B. Gupta, Stamford; Dennis J. Jakiela, Orange; Sampath Venimadhavan; Russell C. Cappadona, both of Norwalk; Venkatrao K. Pai, Stamford, all of CT (US)

(73) Assignee: Cytec Technology Corp., Wilmington, DE (US)

( * ) Notice: Subject to any disclaimer, the term of this patent is extended or adjusted under 35 U.S.C. 154(b) by 0 days.

(21) Appl. No.: 09/388,644

(22) Filed: Sep. 2, 1999

Related U.S. Application Data

(60) Provisional application No. 60/099,176, filed on Sep. 4, 1998.

(51) Int. Cl.[7] ............................................ C07D 251/24
(52) U.S. Cl. ................................. 544/216; 252/403
(58) Field of Search ........................... 544/216; 252/403

(56) References Cited

U.S. PATENT DOCUMENTS

| | | | |
|---|---|---|---|
| 3,118,887 | * 1/1964 | Hardy et al. ............... | 260/248 |
| 3,242,175 | 3/1966 | Duennenberger et al. ........ | 260/248 |
| 3,244,708 | 4/1966 | Duennenberger et al. ........ | 260/248 |
| 3,249,608 | 5/1966 | Biland et al. .............. | 260/248 |
| 3,268,474 | 8/1966 | Hardy et al. ............... | 260/45.8 |
| 3,270,016 | 8/1966 | Duennenberger et al. ........ | 260/48 |
| 3,423,360 | 1/1969 | Huber et al. ............... | 260/47 |
| 4,619,956 | 10/1986 | Susi ....................... | 524/87 |
| 4,740,542 | 4/1988 | Susi ....................... | 524/87 |
| 5,084,570 | 1/1992 | Burdeska et al. ............ | 544/216 |
| 5,106,972 | 4/1992 | Burdeska et al. ............ | 544/219 |
| 5,288,778 | 2/1994 | Schmitter et al. ........... | 524/100 |
| 5,438,138 | 8/1995 | Henneberger et al. ......... | 544/217 |
| 5,461,151 | 10/1995 | Waterman .................. | 544/216 |
| 5,476,937 | 12/1995 | Stevenson et al. ........... | 544/216 |
| 5,478,935 | 12/1995 | Reinehr et al. ............. | 544/180 |
| 5,543,518 | 8/1996 | Stevenson et al. ........... | 544/215 |
| 5,545,836 | 8/1996 | Reinehr et al. ............. | 544/216 |
| 5,591,850 | 1/1997 | Birbaum et al. ............. | 544/216 |
| 5,597,854 | 1/1997 | Birbaum et al. ............. | 524/100 |
| 5,705,643 | 1/1998 | Reinehr et al. ............. | 544/215 |
| 5,726,310 | 3/1998 | Orban et al. ............... | 544/216 |

FOREIGN PATENT DOCUMENTS

| | | |
|---|---|---|
| 480091 | 10/1969 | (CH) . |
| 484695 | 1/1970 | (CH) . |
| 1169947 | 5/1964 | (DE) . |
| 0 444 323 A2/B1 | 9/1991 | (EP) . |
| 0 497 734 A1 | 8/1992 | (EP) . |
| 0 649 841 A1 | 10/1994 | (EP) . |
| 884802 | 12/1961 | (GB) . |
| 1033387 | 6/1966 | (GB) . |
| 9-059263 | 3/1997 | (JP) . |
| WO 94/05645 | 2/1995 | (WO) . |
| WO 96/28431 | 9/1996 | (WO) . |

OTHER PUBLICATIONS

Drahowzal, F. A., in geoge Olah: Friedel–Crafts & relared reactions Chap.XVII, 417–475, 1964.*

Brunetti H and Luthi CE, 1972, "Die synthese von aymmetrisch substituierten o–hydroxyphenyl–s–triazinen", Helv Chimica Acta 55:1566–1595.

Horikoshi Y et al., 1974, "Friedel–Crafts reactions of phenols with cyanuric chloride", Nippon Kagaku Kaishi, 3:530–535.

Tanimoto S and Yamagata M, 1995, "Composition of ultraviolet light absorbers having 2–(hydroxyphenyl)–1,3,5–triazine moiety as the functional group", Senryo To Yakahin (Dyestuffs and Chemicals) 40:325–339.

* cited by examiner

*Primary Examiner*—Richard L. Raymond
*Assistant Examiner*—Venkataraman Balasubramanian
(74) *Attorney, Agent, or Firm*—Pennie & Edmonds LLP

(57) ABSTRACT

Provided is a new process for the preparation of compositions containing at least one triazine ultraviolet light absorber.

17 Claims, No Drawings

PROCESS FOR MAKING 2-(2,4,-DIHYDROXYPHENYL) OR 2-(2,4-DIALKOXYPHENYL)-4,6-BISARYL-1,3,5-TRIAZINES

This application claims the benefit of pending U.S. Provisional Application No. 60/099,176 filed Sep. 4, 1998.

FIELD OF THE INVENTION

This invention relates to a new process for the preparation of 2-(2,4-dihydroxyphenyl)-4,6-bisaryl-1,3,5-triazines or 2-(2,4-dialkoxyphenyl)-4,6-bisaryl-1,3,5-triazines.

BACKGROUND OF THE INVENTION

Exposure to sunlight and other sources of ultraviolet radiation is known to cause degradation of a wide variety of materials, especially polymeric materials. For example, polymeric materials such as plastics often discolor and/or become brittle as a result of prolonged exposure to ultraviolet light. Accordingly, a large body of art has been developed directed towards materials such as ultraviolet light absorbers and stabilizers which are capable of inhibiting such degradation.

A class of materials known to be ultraviolet light absorbers are triazines. Triazine ultraviolet light absorbers are a class of compounds which have at least one 2-hydroxyphenyl substituent on the 1,3,5-triazine ring.

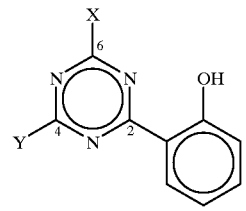

2-(2-Hydroxyphenyl)-1,3,5-triazines
X, Y = substituents

Trisaryltriazine ultraviolet light absorbers are compounds which have aromatic substituents at the 2-, 4- and 6-positions of the 1,3,5-triazine ring, and in which at least one of the aromatic rings has a hydroxyl substituent at the ortho position. These aromatic rings may contain other substituents or may be fused polyaromatics. In general this class of compounds is well known in the art. Disclosures of a number of such trisaryl-1,3,5-triazines, as well as processes for preparing and uses thereof, can be found in the following publications, all of which are incorporated by reference as if fully set forth herein: U.S. Pat. Nos. 3,118,887, 3,242,175, 3,244,708, 3,249,608, 3,268,474, 3,423,360, 4,619,956, 4,740,542, 5,084,570, 5,288,778, 5,461,151, 5,476,937, 5,478,935, 5,543,518, 5,545,836, 5,591,850, and 5,597,854, British patent 1,033,387, Swiss patents 480,091 and 484,695, European patent applications 0,444,323 and 0,649,841, and PCT applications WO94/05645 and WO96/28431.

A commonly used class of trisaryl-1,3,5-triazine ultraviolet light absorbers is based on 2-(2,4-dihydroxyphenyl)-4,6-bisaryl-1,3,5-triazines. In these compounds two non-phenolic aromatic groups and one phenolic aromatic group are attached to the 1,3,5-triazine. The phenolic aromatic group is derived from resorcinol.

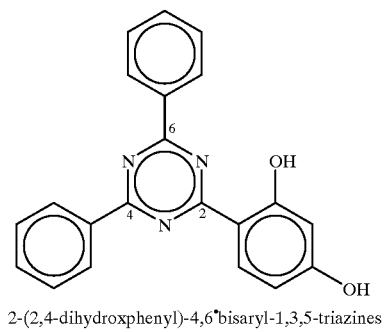

2-(2,4-dihydroxphenyl)-4,6-bisaryl-1,3,5-triazines

Of this class of compounds, a number of commercial examples exist in which the para-hydroxyl group of the phenolic ring is functionalized and the non-phenolic aromatic rings are either unsubstituted phenyl, as in TINUVIN 1577 or meta-xylyl, as in CYASORB UV-1164, CYASORB UV-1164L and TINUVIN 400. These ultraviolet light absorbers exhibit high inherent light stability and permanence as compared to other classes of ultraviolet light absorbers such as benzotriazoles and benzophenones.

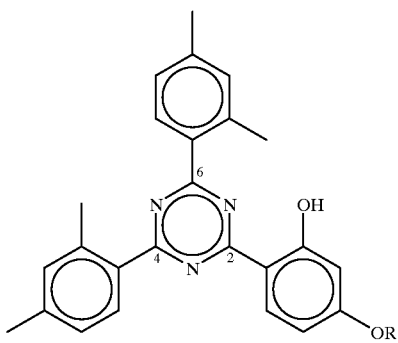

Cyasorb UV 1164: R = n-$C_8H_{17}$
Cyasorb UV 1164 (L): R = iso-$C_8H_{17}$
Tinuvin 400: R = $CH_2CH(OH)CH_2OC_NH_{2N+1}$

N = 12–14

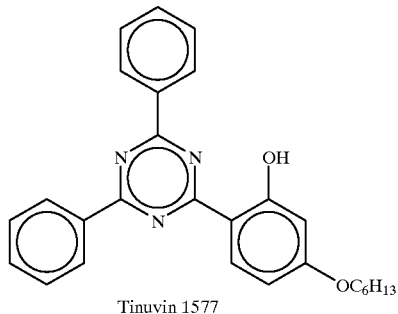

Tinuvin 1577

Several approaches to the production of 2-(2,4-dihydroxyphenyl)-4,6-bisaryl-1,3,5-triazines have been reported in the literature. For example, H. Brunetti and C. E. Luethi, *Helvetica Chimica Acta,* vol. 55, pages 1566–1595 (1972), and S. Tanimoto and M. Yamagata, *Senryo to Yakahin,* vol. 40 (12), pages 325–339 (1995).

The majority of the approaches are based on cyanuric chloride, a readily available and inexpensive starting material. Resorcinol is known to be much more reactive than meta-xylene toward cyanuric chloride, and in Y. Horikoshi et al, *Nippon Kagaku Kaishi* (3), pages 530–535, (1974), CA 81:152177 it has been reported to form only the bis-resorcinol-monochloro-triazine and/or trisresorcinol triazine even when cyanuric chloride to resorcinol were used in equimolar ratios. U.S. Pat No. 3,270,016 describes the formation of bis-resorcinol monochloro triazine in good yield by reacting cyanuric chloride and resorcinol at about equimolar ratio at room temperature for 10 hours, with no mention of the formation of the mono-resorcinol bischloro triazine. Further, German patent application DE 1,169,947 or GB 884802 as mentioned in U.S. Pat No. 5,726,310, describes uncontrolled exothermic reaction when cyanuric chloride, meta-xylene and aluminum chloride are simultaneously introduced.

In one method, shown below, cyanuric chloride is reacted with aromatic compounds, such as meta-xylene, in the presence of aluminum chloride. The reaction produces a monochloro-bisaryl-1,3,5-triazine, which is then reacted with resorcinol in a second step to form a 2-(2,4-dihydroxyphenyl)-4,6-bisaryl-1,3,5-triazine. This process contains several limitations which relate to the first step of the reaction, namely that the first step is not selective and leads to a mixture of all of the possible products, plus unreacted cyanuric chloride. This means that the desired monochloro-bisaryl-1,3,5-triazine must be separated from the reaction mixture before the second reaction step takes place. Another disadvantage is that the first reaction step is not generally applicable to all aromatic compounds. It is well known in the literature that the use of this process gives a useful yield of the desired monochloro-bisaryl-1,3,5-triazine intermediate only when meta-xylene is the aromatic reactant. With other aromatic species, an inseparable mixture of all possible products is formed, and no selectivity for the desired monochloro-bisaryl-1,3,5-triazine is seen. See *Brunelli,* page 1575. For the meta-xylene based product, an improved process has recently been disclosed in U.S. Pat. No. 5,726,310, in which the monochloro-bis(2,4-dimethylphenyl)-1,3,5-triazine intermediate produced in the first reaction step is not isolated, but is further reacted with resorcinol in a one-pot, two-step process. This process contains the disadvantage not only of its being applicable only to meta-xylene, but also that it is a two-step process.

SCHEME 1

Step 1:

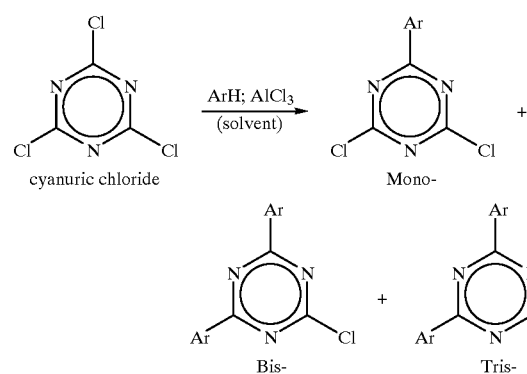

Step 2:

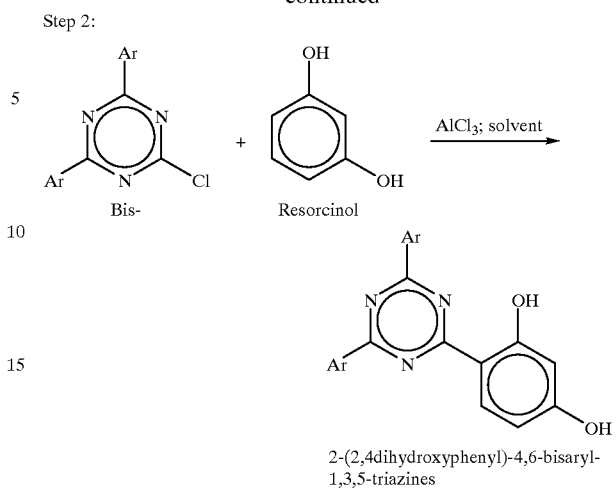

2-(2,4dihydroxyphenyl)-4,6-bisaryl-1,3,5-triazines

In another approach, shown below, cyanuric chloride is reacted with an aryl magnesium halide to prepare a monochloro bisaryl triazine in the first step. The substituted triazine intermediate is isolated and subsequently reacted with resorcinol to produce a 2-(2,4-dihydroxyphenyl)-4,6-bisaryl-1,3,5-triazine. It has been reported that this approach is not selective for the monochloro-bisaryl triazine, for example, *Brunetti,* page 1575. However, modifications with better results have been reported, as in U.S. Pat No. 5,438, 138. While this approach is generally applicable to many aromatic species, it has the disadvantages of being unsuitable for industrial scale production due to the use of a highly reactive Grignard reagent, and uneconomical due to the special precautions associated with the use of Grignard reagents, and the cost of the raw materials used in these compounds.

SCHEME 2

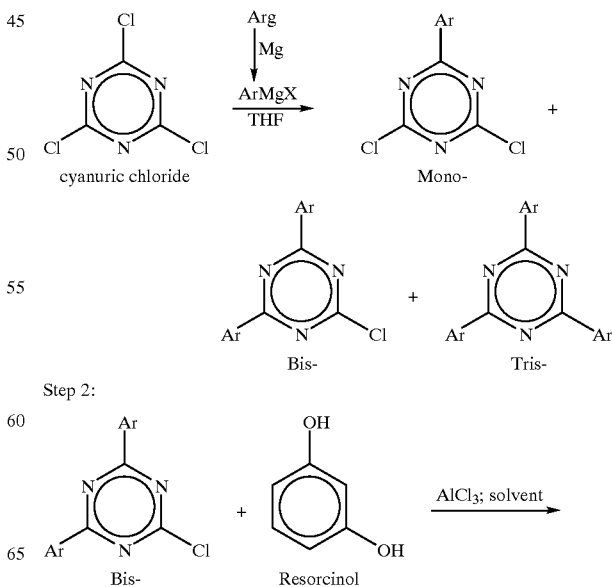

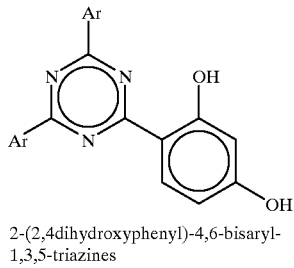

2-(2,4dihydroxyphenyl)-4,6-bisaryl-1,3,5-triazines

Alternative approaches have been developed to address the selectivity problem. In one approach, shown below, cyanuric chloride is first reacted with one equivalent of an alcohol to produce, with high selectivity, a monoalkoxy-bischlorotriazine. This substituted triazine is then reacted in a second step with aromatics in the presence of aluminum chloride to prepare monoalkoxy/hydroxy-bisaryltriazines. These intermediates are then converted to monochloro-bisaryltriazines by reaction with thionyl chloride or phosphorus pentachloride. The monochloro-bisaryltriazines are finally reacted with resorcinol in a fourth step to prepare the desired 2-(2,4-dihydroxyphenyl)-4,6-bisaryl-1,3,5-triazine. This approach can be applied generally to aromatic species, and the desired product is formed with selectivity, but the addition of several steps in the synthesis makes this process economically unattractive.

SCHEME 3

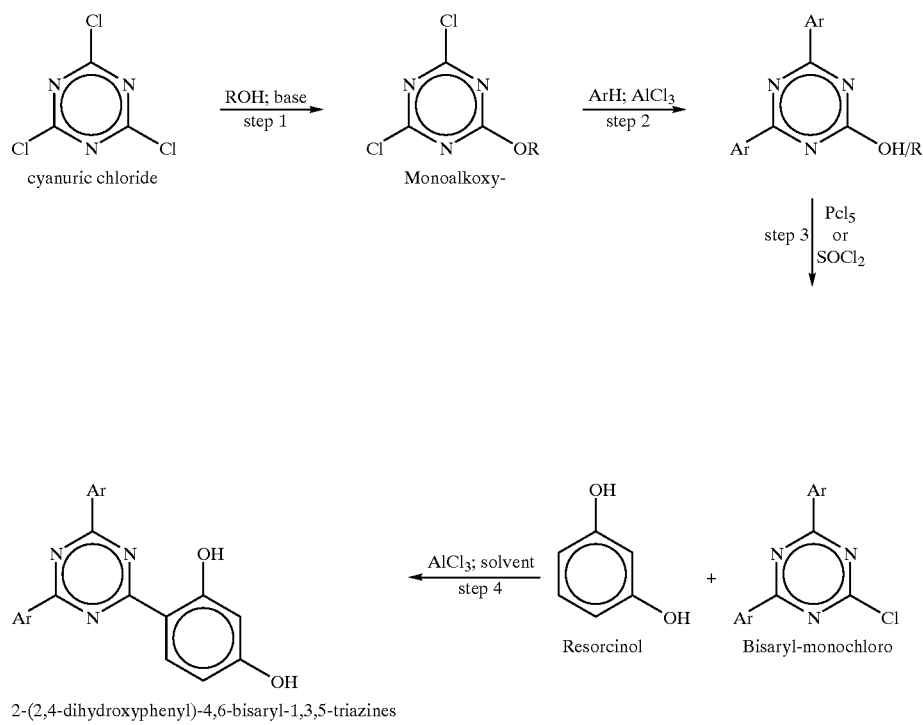

A similar approach is described in U.S. Pat. No. 5,106,972 and U.S. Pat. No. 5,084,570, and is shown below. Cyanuric chloride is first reacted with one equivalent of alkanethiol instead of alcohol. The remaining steps are the same as those described in the previous example. As before, the disadvantage of this approach lies in the additional steps of the synthesis.

SCHEME 4

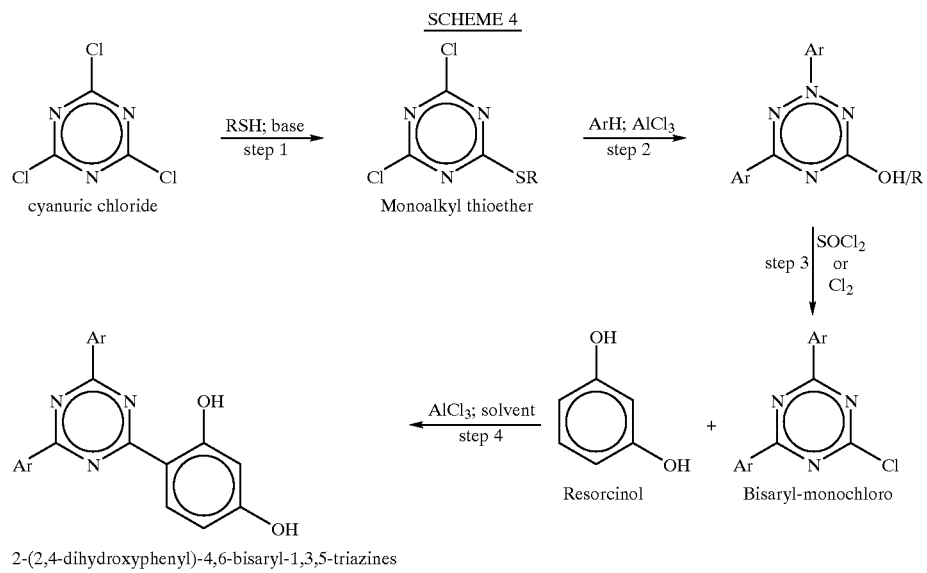

A modification of this approach is disclosed in Japanese patent application 09-059,263. In this process, cyanuric chloride is first reacted with one equivalent of a substituted phenol, such as para-chlorophenol, in the presence of aluminum chloride to produce the oxygen-linked monophenoxy derivative of cyanuric chloride. This intermediate is subsequently reacted with an aromatic, such as meta-xylene, and aluminum chloride to prepare 2-monophenoxy-4,6-bisaryl-1,3,5-triazine, which is subsequently reacted with resorcinol and aluminum chloride in a third step to produce a 2-(2,4-dihydroxyphenyl)-4,6-bisaryl-1,3,5-triazine. This one-pot, three-step process claims an improved yield of the desired product. However, this method has the disadvantage of the need to use para chlorophenol, a toxic chemical, and the need to remove it from the desired product.

SCHEME 5

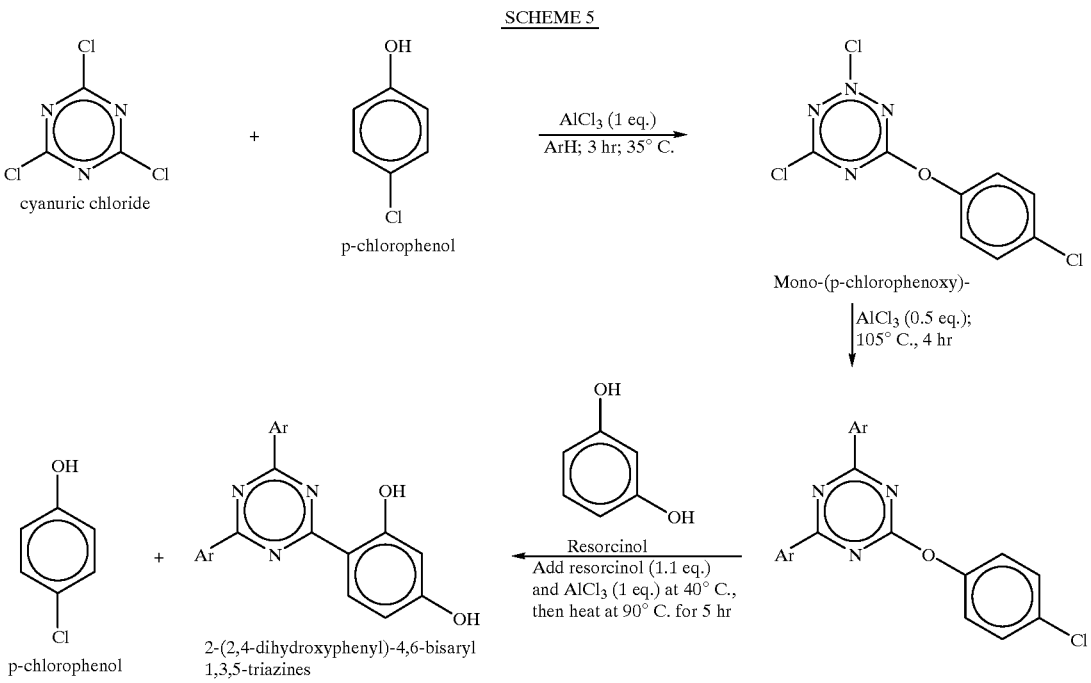

A further approach to the production of 2-chloro-4,6-bisaryl-1,3,5-triazines is disclosed in European patent application 0,497,734. This process involves reacting benzamidine hydrochloride with a chloroformate and dimerizing the product. The resultant 2-hydroxy-4,6-bisaryl-1,3,5-triazine is converted to 2-chloro-4,6-bisaryl-1,3,5-triazine by treatment with thionyl chloride, and finally reaction with resorcinol to produce the 2-(2,4-dihydroxyphenyl)-4,6-bisaryl-1,3,5-triazine. This method also has the disadvantage of using para-chlorophenol, a toxic chemical. Further the multi-step synthesis renders the process uneconomical for industrial use.

SCHEME 6

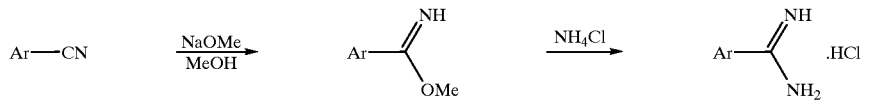

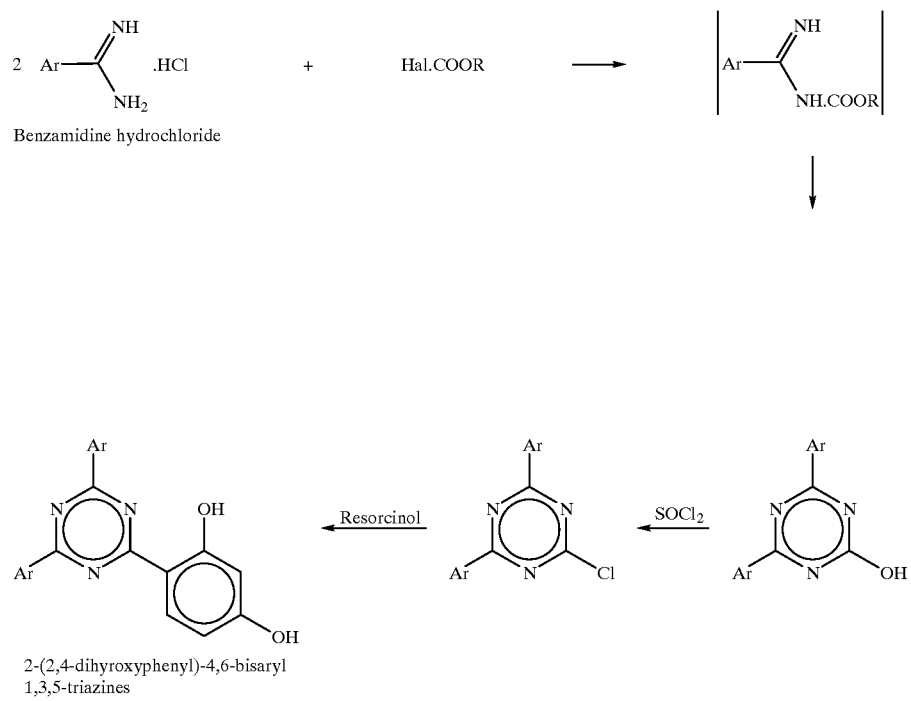

In addition to the approaches described above, other approaches exist which utilize benzonitriles or benzamidines as the starting material. The use of 2,4-dihydroxybenzaldehyde, phenyl (or alkyl) 2,4-dihydroxybenzoates and 2-aryl-1,3-benzoxazine-4-ones is shown below, and is disclosed in, for example, U.S. Pat. Nos. 5,705,643 and 5,478,935 and PCT application WO96/

28431. These approaches have the disadvantages of the starting materials being expensive, and the possible need for additional synthetic steps in the preparation.

SCHEME 7
Based on Benzamidine reactions with 2,4-dihydroxybenzaldehyde:

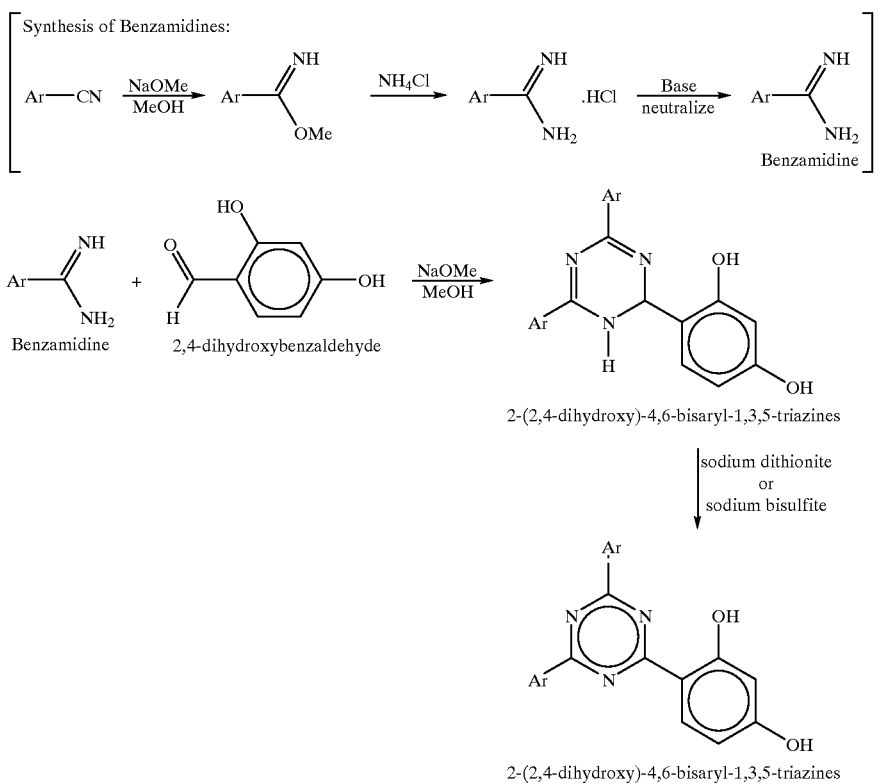

SCHEME 8
Based on Benzamidine reactions with Phenyl 2,4-dihydroxybenzoate:

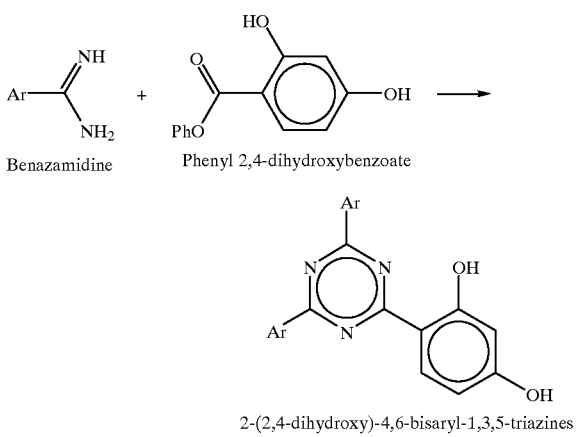

SCHEME 9
Based on Benzamidine reactions with substituted 2-aryl-1,3-benzoxazin-4-ones:

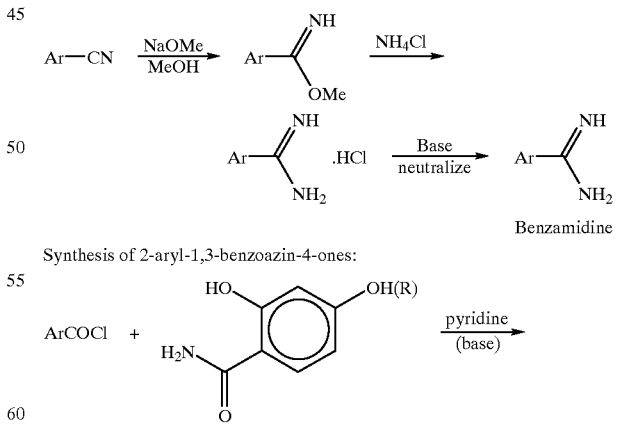

-continued

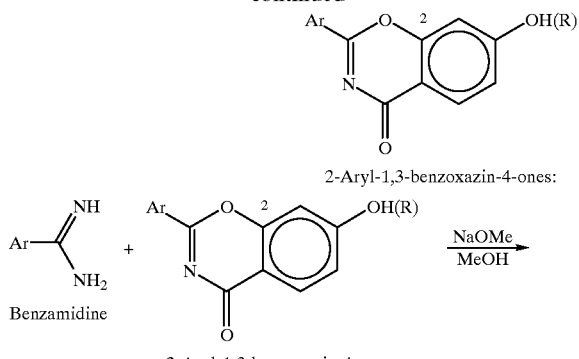

2-Aryl-1,3-benzoxazin-4-ones:

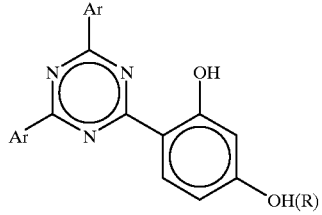

2-(2,4-dihydroxy)-4,6-bisaryl-1,3,5-triazines

It can be seen that a need exists for a novel method of production of 2-(2,4-dihydroxyphenyl)-4,6-bisaryl-1,3,5-triazines which is highly selective, economical, having minimal synthetic steps and need for isolation of the intermediate, and demonstrates improved safety to the chemist and to the environment. It is the object of this invention to provide such a novel method of production.

SUMMARY OF THE INVENTION

The invention provides a process for preparing compositions containing at least one triazine compound. In particular, the present invention relates to a novel process for the production of a composition comprising at least one triazine compound of Formula A:

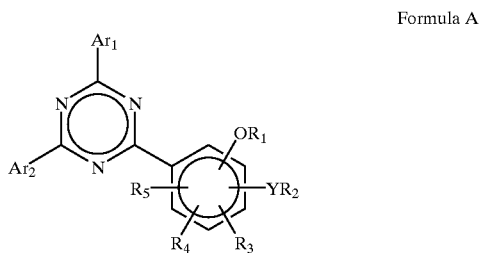

Formula A wherein $R_1$, $R_2$, $R_3$, $R_4$ and $R_5$ are the same or different and each is hydrogen, halogen, alkyl of 1 to 24 carbon atoms, haloalkyl of 1 to 24 carbon atoms, alkenyl of 2 to 24 carbon atoms, acyl of 1 to 24 carbon atoms, aryl of 6 to 24 carbon atoms, cycloalkyl of 5 to 24 carbon atoms, cycloacyl of 5 to 24 carbon atoms, aralkyl of 7 to 24 carbon atoms, aracyl of 6 to 24 carbon atoms, OR, NRR', CONRR', OCOR, CN, SR, $SO_2R$, $SO_3H$, $SO_3M$, wherein M is an alkali metal, R and R' are the same or different and each is hydrogen, alkyl of 1 to 24 carbon atoms, haloalkyl of 1 to 24 carbon atoms, alkenyl of 2 to 24 carbon atoms, acyl of 1 to 24 carbon atoms, aryl of 6 to 24 carbon atoms, cycloalkyl of 5 to 24 carbon atoms, cycloacyl of 5 to 24 carbon atoms, aralkyl of 7 to 24 carbon atoms, or aracyl of 6 to 24 carbon atoms, optionally with either of $R_3$ and $R_4$, or $R_4$ and $R_5$, taken together being a part of a saturated or unsaturated fused carbocyclic ring optionally containing O, N or S atoms in the ring, and Y is a direct bond, O, NR", or SR", wherein R" is hydrogen, alkyl of 1 to 24 carbon atoms, haloalkyl of 1 to 24 carbon atoms, alkenyl of 2 to 24 carbon atoms, acyl of 1 to 24 carbon atoms, aryl of 6 to 24 carbon atoms, cycloalkyl of 5 to 24 carbon atoms, cycloacyl of 5 to 24 carbon atoms, aralkyl of 7 to 24 carbon atoms or aracyl of 6 to 24 carbon atoms; and $Ar_1$ and $Ar_2$ are the same or different, and each independently is a radical of a compound of Formula B:

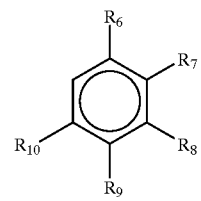

Formula B wherein $R_6$, $R_7$, $R_8$, $R_9$ and $R_{10}$ are the same or different and each is hydrogen, halogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, aralkyl of 7 to 24 carbon atoms, aracyl of 6 to 24 carbon atoms, OR, NRR', CONRR', OCOR, CN, SR, $SO_2R$, $SO_3H$, $SO_3M$, wherein M is an alkali metal, R and R' are the same or different and each is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 5 to 24 carbon atoms, cycloacyl of 5 to 24 carbon atoms, aralkyl of 7 to 24 carbon atoms, or aracyl of 6 to 24 carbon atoms, and optionally with either of $R_6$ and $R_7$ taken together, $R_7$ and $R_8$ taken together, $R_8$ and $R_9$ taken together, or $R_9$ and $R_{10}$ taken together being a part of a saturated or unsaturated fused carbocyclic ring optionally containing O, N or S atoms in the ring, which process comprises:

simultaneously reacting in the presence of a catalyst, sufficient amounts of a compound of Formula C:

Formula C wherein X is a halogen, a compound of Formula D:

Formula D wherein Y, $R_1$, $R_2$, $R_3$, $R_4$ and $R_5$ are as described above, and a compound of Formula E:

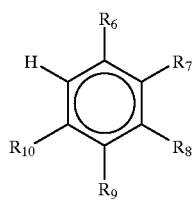

Formula E wherein $R_6$, $R_7$, $R_8$, $R_9$ and $R_{10}$ are as described above, at a suitable temperature and pressure, and for a time sufficient to produce a reaction mixture comprising the composition.

The present invention relates to a process for the production of a composition comprising at least one triazine compound of Formula A:

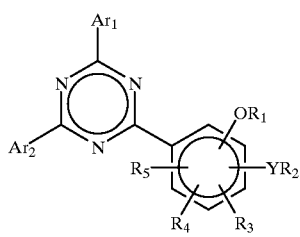

Formula A wherein $R_1$, $R_2$, $R_3$, $R_4$ and $R_5$ are the same or different and each is hydrogen, halogen, alkyl of 1 to 24 carbon atoms, haloalkyl of 1 to 24 carbon atoms, alkenyl of 2 to 24 carbon atoms, acyl of 1 to 24 carbon atoms, aryl of 6 to 24 carbon atoms, cycloalkyl of 5 to 24 carbon atoms, cycloacyl of 5 to 24 carbon atoms, aralkyl of 7 to 24 carbon atoms, aracyl of 6 to 24 carbon atoms, OR, NRR', CONRR', OCOR, CN, SR, $SO_2R$, $SO_3H$, $SO_3M$, wherein M is an alkali metal, R and R' are the same or different and each is hydrogen, alkyl of 1 to 24 carbon atoms, haloalkyl of 1 to 24 carbon atoms, alkenyl of 2 to 24 carbon atoms, acyl of 1 to 24 carbon atoms, aryl of 6 to 24 carbon atoms, cycloalkyl of 5 to 24 carbon atoms, cycloacyl of 5 to 24 carbon atoms, aralkyl of 7 to 24 carbon atoms, or aracyl of 6 to 24 carbon atoms, optionally with either of $R_3$ and $R_4$, or $R_4$ and $R_5$, taken together being a part of a saturated or unsaturated fused carbocyclic ring optionally containing O, N or S atoms in the ring, and Y is a direct bond, O, NR", or SR", wherein R" is hydrogen, alkyl of 1 to 24 carbon atoms, haloalkyl of 1 to 24 carbon atoms, alkenyl of 2 to 24 carbon atoms, acyl of 1 to 24 carbon atoms, aryl of 6 to 24 carbon atoms, cycloalkyl of 5 to 24 carbon atoms, cycloacyl of 5 to 24 carbon atoms, aralkyl of 7 to 24 carbon atoms or aracyl of 6 to 24 carbon atoms; and $Ar_1$ and $Ar_2$ are the same or different, and each independently is a radical of a compound of Formula B:

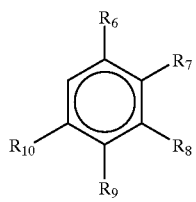

Formula B wherein $R_6$, $R_7$, $R_8$, $R_9$ and $R_{10}$ are the same or different and each is hydrogen, halogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, aralkyl of 7 to 24 carbon atoms, aracyl of 6 to 24 carbon atoms, OR, NRR', CONRR', OCOR, CN, SR, $SR_2R$, $SO_3H$, $SO_3M$, wherein M is an alkali metal, R and R' are the same or different and each is hydrogen, alkyl of 1 to 24 carbon atoms, haloalkyl of 1 to 24 carbon atoms, aryl of 6 to 24 carbon atoms, alkenyl of 2 to 24 carbon atoms, acyl of 1 to 24 carbon atoms, cycloalkyl of 5 to 24 carbon atoms, cycloacyl of 5 to 24 carbon atoms, aralkyl of 7 to 24 carbon atoms, or aracyl of 6 to 24 carbon atoms, and optionally with either of $R_6$ and $R_7$ taken together, $R_7$ and $R_8$ taken together, $R_8$ and $R_9$ g taken together, or $R_9$ and $R_{10}$ taken together being a part of a saturated or unsaturated fused carbocyclic ring optionally containing O, N or S atoms in the ring, which process comprises:

simultaneously reacting in the presence of a catalyst, sufficient amounts of a compound of Formula C:

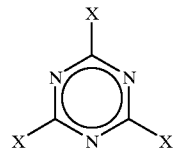

Formula C wherein X is a halogen, a compound of Formula D:

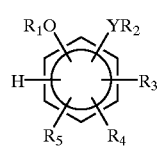

Formula D wherein Y, $R_1$, $R_2$, $R_3$, $R_4$ and $R_5$ are as described above, and a compound of Formula E:

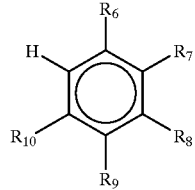

Formula E wherein $R_6$, $R_7$, $R_8$, $R_9$ and $R_{10}$ are as described above, at a suitable temperature and pressure, and for a time sufficient to produce a reaction mixture comprising the composition.

This result is unexpected, since theoretically, a statistical distribution of several products would be expected to be produced from such a simultaneous reaction. A preferred embodiment of the present invention is a process for the preparation of 2-(2,4-dihydroxyphenyl)-4,6-bis(2,4-dimethylphenyl)-1,3,5-triazine,

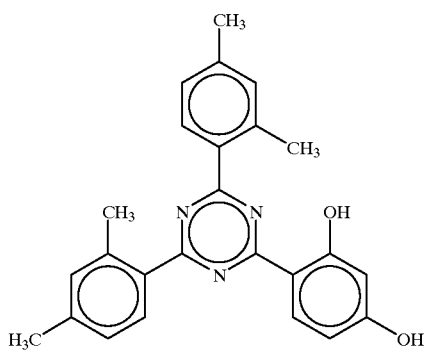

which comprises simultaneously reacting in the presence of a catalyst, sufficient amounts of a cyanuric halide, preferably cyanuric chloride; meta-xylene and resorcinol, at a suitable temperature and pressure, and for a time sufficient to produce a reaction mixture comprising the composition. The formation of the mono-resorcinol containing triazine product as the major product, with the bis-resorcinol containing triazine product formed in small amounts is contrary to expectation.

The process of the present invention is a one-pot, one-step process which avoids the need to sustain the reaction mixture at different temperatures for long periods. No significant exotherm is produced in the reaction, despite the fact that all reactants are introduced simultaneously. The fact that no significant exotherm is observed is in contrast to the prior art, which describes uncontrolled exothermic reaction when cyanuric chloride, meta-xylene and aluminum chloride are simultaneously introduced. Thus the process of the present invention discloses a simultaneous reaction of cyanuric chloride with aromatic species and resorcinol, which can be carried out at a relatively low temperature, with no associated safety risks.

Suitable solvents for use in the process of the present invention are aliphatic hydrocarbons, halogenated aliphatic and aromatic compounds, aliphatic and aromatic nitro compounds and carbon disulfide. Preferred solvents are halogenated solvents such as chlorobenzene, dichlorobenzene and 1,1,2,2-tetrachloroethane.

The catalyst used in the process of the present invention is a Lewis acid catalyst. Preferred catalysts are aluminum trihalides. The most preferred catalyst is aluminum chloride.

The process of the present invention may be carried out by combining the reactants in the reactor and bringing about the reaction. The reaction takes place at a temperature of between about 0° C. to about 120° C. A preferred temperature range is between about 0° C. to about 90° C. The most preferred temperature range is between about 10° C. to about 60° C.

The amount of catalyst used is between about 1.5 to about 4 equivalents based upon the amount of the compound of Formula C. More preferably the amount of catalyst used is between about 2 to about 3.5 equivalents based upon the amount of the compound of Formula C. Most preferably the amount of catalyst used is between about 2.25 to 2.75 equivalents based upon the amount of the compound of Formula C.

The amount of compound of Formula B used is between about 1.9 to 2.5 equivalents based upon the amount of the compound of Formula C.

The amount of compound of Formula D used is between about 0.5 to 1.5 equivalents based upon the amount of the compound of Formula C. More preferably the amount of compound of Formula D used is between about 0.9 to 1.1 equivalents based upon the amount of the compound of Formula C.

The compounds used in the process of the present invention can be added to the reaction vessel in any sequence. The preferred time for the reaction is between about 2 to about 24 hours.

Uses of Triazines

The triazines of the present invention are particularly useful as ultraviolet light absorber agents for stabilizing a wide variety of materials including, for example, various polymers (both crosslinked and thermoplastic), photographic materials and dye solutions for textile materials, as well as in ultraviolet light screening agents (such as sunscreens). The triazines of the present invention can be incorporated into such material in any one of a variety of conventional manners, including for example, physical mixing or blending, optionally, with chemical bonding to the material (typically to a polymer), as a component in a light stabilizing composition such as a coating or solution, or as a component in a UV screening composition such as a sunscreen composition.

The triazines of the present invention can be employed to stabilize materials which are subject to degradation by ultraviolet radiation by incorporating the presently claimed compounds into polymeric materials, either chemically or physically. Non-limiting examples of polymeric materials that may be so stabilized are polyolefins, polyesters, polyethers, polyketones, polyamides, natural and synthetic rubbers, polyurethanes, polystyrenes, high-impact polystyrenes, polyacrylates, polymethacrylates, polyacetals, polyacrylonitriles, polybutadienes, polystyrenes, ABS, SAN (styrene acrylonitrile), ASA (acrylate styrene acrylonitrile), cellulosic acetate butyrate, cellulosic polymers, polyimides, polyamideimides, polyetherimides, polyphenylsulfide, PPO, polysulfones, polyethersulfones, polyvinylchlorides, polycarbonates, polyketones, aliphatic polyketones, thermoplastic TPU's, aminoresin crosslinked polyacrylates and polyesters, polyisocyanate crosslinked polyesters and polyacrylates, phenol/formaldehyde, urea/formaldehyde and melamine/formaldehyde resins, drying and non-drying alkyd resins, alkyd resins, polyester resins, acrylate resins cross-linked with melamine resins, urea resins, isocyanates, isocyanurates, carbamates, and epoxy resins, cross-linked epoxy resins derived from aliphatic, cycloaliphatic, heterocyclic and aromatic glycidyl compounds, which are cross-linked with anhydrides or amines, polysiloxanes, Michael addition polymers, amines, blocked amines with activated unsaturated and methylene compounds, ketimines with activated unsaturated and methylene compounds, polyketimines in combination with unsaturated acrylic polyacetoacetate resins, polyketimines in combination with unsaturated acrylic resins, radiation curable compositions, epoxymelamine resins, organic dyes, cosmetic products, cellulose-based paper formulations, photographic film paper, ink, and blends thereof.

Further non-limiting examples of specific polymers which may be stabilized include:

1. Homo- and copolymers of monoolefins and diolefins including but not limited to ethylene, propylene, isobutylene, butene, methylpentene, hexene, heptene, octene, isoprene, butadiene, hexadiene, dicyclopentadiene, ethylidene and cycloolefins such as cyclopentene and norbornene; for example, polyethylenes (which optionally can be crosslinked) such as high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE) and branched low density polyethylene (BLDPE).
2. Copolymers of one or more monoolefins and/or diolefins with carbon monoxide and/or with other vinyl monomers, including limited acrylic and methacrylic acid, acrylates and methacrylates, acrylamides, acrylonitriles, styrenes, vinyl acetate (such as ethylene/vinyl acetate copolymers), vinyl halides, vinylidene halides, maleic anhydride and allyl monomers such as allyl alcohol, allyl amine ally glycidyl ether and derivatives thereof.
3. Hydrocarbon resins (such as $C_5$–$C_9$) including hydrogenated modifications thereof and mixtures of polyalkylenes and starch.
4. Homo- and copolymers of styrenes such as styrene, p-methylstyrene and α-methylstyrene.
5. Copolymers of one or more styrenes with other vinyl monomers such as olefins and diolefins (e.g., ethylene, isoprene and/or butadiene), acrylic and methacrylic acid, acrylates and methacrylates, acrylamides, acrylonitriles, vinyl acetate (such as ethylene/vinyl acetate copolymers), vinyl halides, vinylidene halides, maleic anhydride and allyl compounds such as allyl alcohol, allyl amine allyl glycidyl ether and derivatives thereof.
6. Graft copolymers of styrenes on polybutadienes, polybutadiene/styrene copolymers and polybutadiene/acrylonitrile copolymers; styrene (or α-methylstyrene) and acrylonitrile (or methacrylonitrile) on polybutadiene; styrene and maleic anhydride on polybutadiene; styrene, acrylonitrile and maleic anhydride or maleimide on polybutadiene; styrene and acrylonitrile on ethylene/propylene/diene copolymers; styrene and acrylonitrile on polyalkyl acrylates or methacrylates; and styrene and acrylonitrile on acrylate/butadiene copolymers.
7. Halogen-containing polymers such as polychloroprene; chlorinated rubbers; chlorinated and brominated isobutylene/isoprene copolymers; chlorinated or sulfochlorinated polyethylene; copolymers of ethylene and chlorinated ethylene; epichlorohydrin polymers and copolymers; and polymers and copolymers of halogen-containing vinyl compounds such as vinyl chloride, vinylidene chloride, vinyl fluoride and/or vinylidene fluoride and other vinyl monomers.
8. Homo- and copolymers derived from α, β-unsaturated acids and derivatives thereof such as acrylic acid, methacrylic acid, acrylates, methacrylates, acrylamides and acrylonitriles.
9. Copolymers of the monomers mentioned in (8) with other unsaturated monomers such as olefins and diolefins (e.g., butadiene), styrenes, vinyl halides, maleic anhydride and allyl monomer such as allyl alcohol, allyl amine, allyl glycidyl ether and derivatives thereof.
10. Homo- and copolymers derived from unsaturated alcohols and amines or the acyl derivatives or acetals thereof, such as vinyl alcohol, vinyl acetate, vinyl stearate, vinyl benzoate, vinyl maleate, vinyl butyral, allyl alcohol, allyl amine, allyl glycidyl ether, allyl phthalate and allyl melamine; as well as copolymers of such monomers with other ethylenically unsaturated monomers mentioned above.

For the preceding polymer groups 1–10, the present invention includes these polymers as prepared by metallocene catalysts.

11. Homo- and copolymers of cyclic ethers such as alkylene glycols and alkylene oxides, as well as copolymers with bisglycidyl ethers.
12. Polyacetals such as polyoxymethylene and those polyoxymethylenes which contain ethylene oxide as a comonomer; and polyoxymethylenes modified with thermoplastic polyurethanes, acrylates and/or MBS.
13. Polyphenylene oxides and sulfides.
14. Polyurethanes derived from hydroxy-functional components such as polyhydric alcohols, polyethers, polyesters, polyacrylics and/or polybutadienes on the one hand, and aliphatic and/or aromatic isocyanates on the other, as well as precursors thereof.
15. Polyamides and copolyamides derived from diamines, dicarboxylic acids and/or aminocarboxylic acids or the corresponding lactams, such as polyamide 4, polyamide 6, polyamide 6/6, polyamide 6/10, polyamide 6/9, polyamide 6/12, polyamide 4/6, polyamide 12/12, polyamide 11 and polyamide 12; aromatic polyamides starting from m-xylene diamine and adipic acid; polyamides prepared from hexamethylene diamine and isophthalic and/or terephthalic acid and with or without an elastomer as a modifier, for example, poly-2,4,4-trimethylhexamethylene terephthalamide or poly-m-phenylene isophthalamide; block copolymers of the aforementioned polyamides with polyolefins, olefin copolymer, ionomers, chemically bonded or grafted elastomers, or polyethers such as polyethylene glycol, polypropylene glycol or polytetramethylene glycol; and polyamides condensed during processing (RIM polyamide systems).
16. Polyureas, polyimides, polyamide-imides, polyetherimides, polyesterimides, polyhydantoins and polybenzimidazoles.
17. Polyesters derived from dicarboxylic acids, diols and/or hydroxycarboxylic acids or the corresponding lactones, such as polyethylene terephthalate, polybutylene terephthalate, poly-1,4-dimethylcyclohexane terephthalate and polyhydroxybenzoates, as well as block copolyether esters derived from hydroxyl-terminated ethers; PETG; PEN; PTT; and also polyesters modified with polycarbonate or MBS.
18. Polycarbonates and polyester carbonates.
19. Polysulfones, polyether sulfones and polyether ketones.
20. Crosslinked polymers derived from aldehydes condensation resins such as phenol/formaldehyde resins, urea/formaldehyde resins and melamine/formaldehyde resins.
21. Drying and non-drying alkyd resins.
22. Unsaturated polyester resins derived from copolyesters of saturated and unsaturated dicarboxylic acids with polyhydric alcohols and vinyl compounds as crosslinking agents and also halogen-containing modifications thereof.
23. Crosslinkable acrylic resins derived from substituted acrylates such as epoxy acrylates, hydroxy acrylates, isocyanato acrylates, urethane acrylates or polyester acrylates.
24. Alkyd resins, polyester resins and acrylate resins crosslinked with melamine resins, urea resins, isocyanates, isocyanurates, carbamates or epoxy resins.
25. Crosslinked epoxy resins derived from aliphatic, cycloaliphatic, heterocyclic and/or aromatic glycidyl compounds such as bisphenol A and bisphenol F, which are crosslinked with customary hardeners such as anhydrides or amines.
26. Natural polymers such as cellulose, rubber, gelatin and chemically modified homologous derivatives thereof, including cellulose acetates, cellulose propionates and cellulose butyrates, or the cellulose ethers such as methyl cellulose, as well as rosins and their derivatives.
27. Polysiloxanes.
28. Michael addition polymers of amines or blocked amines (e.g., ketimines) with activated unsaturated and/or methylene compounds such as acrylates and methacrylates, maleates and acetoacetates.
29. Mixtures or blends of any of the above, such as PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylate, POM/thermoplastic PUR, PC/thermoplastic polyurethane, POM/acrylate, POM/MBS, PPO/HIPS, PPO/PA6.6 and copolymers, PA/HDPE, PP/HDPE, PP/LDPE, LDPE/HDPE, LDPE/EVA, LDPE/EAA, PA/PP, PA/PPO, PBT/PC/ABS, PBT/PET/PC and the like.
30. Polyketimines in combination with unsaturated acrylic polyacetoacetate resins or with unsaturated acrylic resins including urethane acrylates, polyether acrylates, vinyl or acryl copolymers with pendant unsaturated groups and acrylated melamines.
31. Radiation curable compositions containing ethylenically unsaturated monomers or oligomers and a polyunsaturated aliphatic oligomer.
32. Epoxymelamine resins such as light-stable epoxy resins cross-linked by an epoxy functional coetherified high solids melamine resin.

Other materials which can be stabilized include, for example:
33. Naturally occurring and synthetic organic materials which may be mixtures of compounds, including mineral oils, animal and vegetable fats, oils and waxes, or oils, fats or waxes based on synthetic esters (e.g., phthalates, adipates, phosphates or trimellitates) and also mixtures of synthetic esters with mineral oils in any ratio.
34. Aqueous emulsions of natural or synthetic rubber such as natural latex or lattices of carboxylated styrene/butadiene copolymers.
35. Organic dyes such as azo dyes (diazo, triazo and polyazo), anthraquinones, benzodifuranones, polycyclic aromatic carbonyl dyes, indigoid dyes, polymethines, styryl dyes, di- and triaryl carbonium dyes, phthalocyanines, quinophthalones, sulfur dyes, nitro and nitroso dyes, stilbene dyes, formazan dyes, quinacridones, carbazoles and perylene tetracarboxylic diimides.
36. Cosmetic products, such as skin lotions, collagen creams, sunscreen, facial make-up, etc., comprising synthetic materials such as antioxidants, preservatives, lipids, solvents, surfactants, colorants, antiperspirants, skin conditioners, moisturizers etc.; as well as natural products such as collagen, proteins, mink oil, olive oil, coconut oil, carnauba wax, beeswax, lanolin, cocoa butter, xanthan gum, aloe, etc.
37. Cellulose-based paper formulations for use, e.g., in newsprint, cardboard, posters, packaging, labels, stationery, book and magazine paper, bond typing paper, multi-purpose and office paper, computer paper, xerographic paper, laser and ink-jet printer paper, offset paper, currency paper, etc.
38. Photographic film paper.
39. Ink.

EXAMPLES

The invention will now be illustrated by the following examples. The examples are not intended to be limiting of the scope of the present invention. In conjunction with the general and detailed descriptions above, the examples provide further understanding of the present invention.

Comparative Example 1

Reaction of Cyanuric Chloride, m-xylene, Resorcinol, and Aluminum Trichloride. Use of 1.0 eq. Aluminum Trichloride

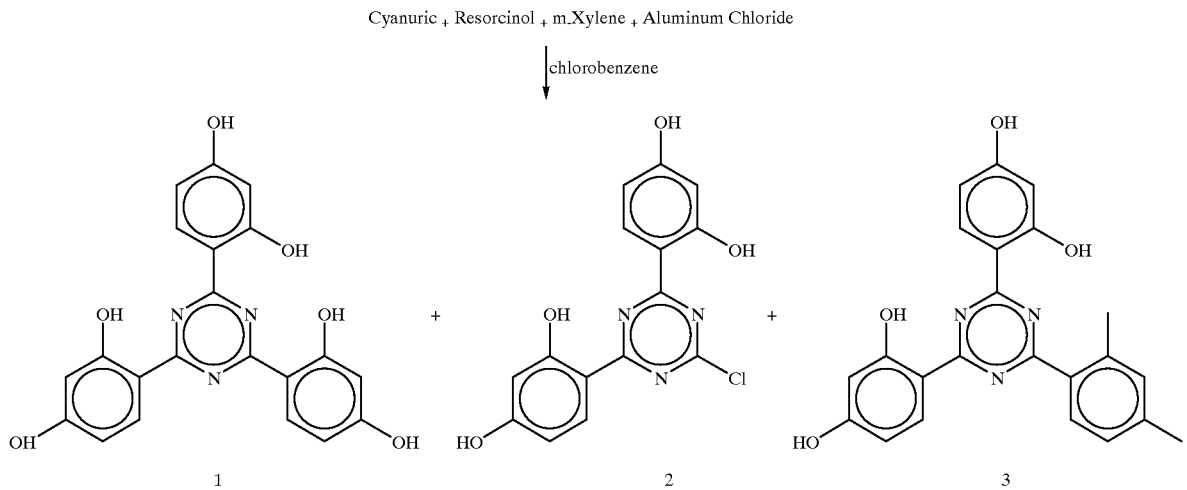

A mixture of 1.84 g cyanuric chloride (10 mmol), 2.12 g of m-xylene (2 eq.), and 1.10 g of resorcinol (1 eq.) in 20 mL chlorobenzene under a nitrogen atmosphere was cooled to 2° C. Aluminum trichloride (2.12 g, 1 eq.) was added over 2 mm. The mixture was then warmed to 35° C. with stirring. After 22 hr., a sample was taken and quenched with ice and dilute aq. HCl. The resulting precipitate was filtered, washed with water, dissolved in tetrahydrofuran and analyzed by HPLC. HPLC analysis (area % at 290 nm) showed mainly tris- and bis-resorcinol containing triazine products 2,4,6-tris-(2,4-dihydroxyphenyl)-s-triazine (1) and 2-chloro-4,6-bis-(2,4-dihydroxyphenyl)-s-triazine (2) with no m-xylyl substitution. The ratio of 1 to 2 was 21:78. Unreacted m-xylene was also present. The only triazine product containing xylene observed was bisresorcinol-triazine based 2,4-bis-(2,4-dihydroxyphenyl)-6-(2,4-dimethylphenyl)-s-triazine 3. The monoresorcinol-triazine based product, 2-(2,4-dihydroxyphenyl)-4,6-bis-(2,4-dimethylphenyl)-s-triazine 4 was not formed.

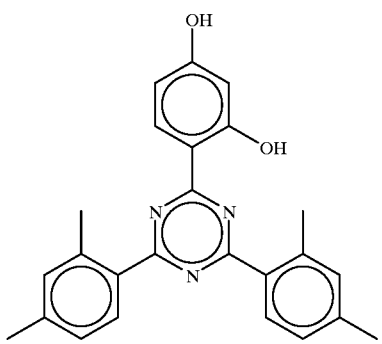

4

The formation of only trisresorcinol-triazine and bisresorcinol-triazine based products is in agreement with the prior art cited before (Y. Horikoshi, et al, *Nippon Kagaku Kaishi* (3), 530–5, 1974; CA 81:152177 and U.S. Pat. No. 3,270,016 (Ex. 6))

Example 1

2-(2,4-Dihydroxyphenyl)-4,6-bis-(2,4-dimethylphenyl)s-triazine (4). Use of 2.5 eq Aluminum Trichloride To a stirring mixture of 1.84 g of cyanuric chloride, 1.1 gm of resorcinol, 2.5 mL of m-xylene and 25 mL of chlorobenzene was added 3.35 g of aluminum chloride (2.5 eq. based on cyanuric chloride) at 5° C. The reaction mixture was stirred at 5° C. for 2 h, then at 15° C. for 4 hr and finally at room temperature for 24 hr. The reaction mixture was analyzed by TLC and HPLC. The HPLC analysis confirmed the formation of 2-(2,4-dihydroxyphenyl)-4,6-(2,4-dimethylphenyl)-1,3,5-triazine (4) and 2,4,6-tris(2,4-dimethylphenyl)-1,3,5-triazine as the only two major products. The bisresorcinol based product, 2,4-bis(2,4-dihydroxyphenyl)-6-(2,4-dimethylphenyl)-1,3,5-triazine (3), was formed only as a minor component and the ratio of 4:3 was 97:3. The 2-chloro-4,6-bis(2,4-dihydroxyphenyl)s-triazine (2) was only 0.36% and 2,4,6-tris-(2,4-dihydroxyphenyl)-s-triazine (1) was 0.5%. The experiment demonstrated the preferential formation of monoresorcinol based product 4 by reacting cyanuric chloride, resorcinol, m-xylene and aluminum chloride simultaneously with higher charge of aluminum chloride.

Example 2

2-(2,4-Dihydroxyphenyl)-4,6-bis-(2,4-dimethylphenyl)-s-triazine (4). Use of 2.25 eq Aluminum Trichloride.

A mixture of 10 g cyanuric chloride (0.0542 mol), 11.51 g of m-xylene (2 eq.), and 5.97 g of resorcinol (1 eq.) in 100 mL chlorobenzene under a nitrogen atmosphere was cooled to 20° C. under a nitrogen atmosphere. Aluminum trichloride (16.26 g, 2.25 eq.) was added over 25 min. such that the temperature was maintained below 5° C. The mixture was then warmed to 25° C. with stirring, and the progress of the reaction was monitored by HPLC (area % at 290 nm). After 24 hr. at 25° C., HPLC analysis showed 37.6% of 2-(2,4-dihydroxyphenyl)-4,6-bis-(2,4-dimethylphenyl)-s-triazine (4) and only 1.0% of 1,4.4% of 2, and 5.1% of 3. Additional m-xylene (2 eq.) and aluminum trichloride (0.25 eq.) were added, and the mixture was heated to 32–35° C. for 20 hr. HPLC analysis indicated that the yield of 1 was increased to 45.3% and there was only 1.9% 2,4,6-tris-(2.4-dihyroxyphenyl)-5-triazine and 5.6% 2,4-bis-(2,4-dihydroxyphenyl)-6-(2,4-dimethylphenyl)-5-triazine.

Example 3

2-(2,4-Dihydroxyphenyl)-4,6-bis(2,4-dimethylphenyl)-s-triazine (4). Use of 2.25 eq Aluminum Trichloride; Initial Reaction Temperature of 35° C.

A mixture of 10 g cyanuric chloride (0.0542 mol), 11.51 g of m-xylene (2 eq.), and 5.97 g of resorcinol (1 eq.) in 100 mL chlorobenzene under a nitrogen atmosphere was cooled to 2° C. Aluminum trichloride (16.26 g, 2.25 eq.) was added over 25 min. such that the temperature was maintained below 5° C. The mixture was then warmed to 35° C. with stirring, and the progress of the reaction was monitored by HPLC (area % at 290 nm). After 23 hr. at 35° C. HPLC analysis showed 47.4% 2-(2,4-dihydroxyphenyl)-4,6-bi5(2,4-dimethylphenyl)-s-triazine (4) and only 7.6% of 2,4-bis-(2,4-dihydroxyphenyl)-6-(2,4-dimethyl-s-triazine (3), with no unreacted cyanuric chloride. Additional m-xylene (28.77 g) and 5.43 g aluminum trichloride (0.75 eq.) were added, and the mixture was heated to 55–60° C. for 24 hr. HPLC analysis indicated that the yield of 1 was increased to 51%.

Example 4

Reaction of Cyanuric Chloride, m-xylene, Resorcinol, and Aluminum Trichloride. Use of 2.0 eq Aluminum Trichloride.

A mixture of 10 g cyanuric chloride (0.0542 mol), 11.51 g of m-xylene (2 eq.), and 5.97 g of resorcinol (1 eq.) in 100 mL chlorobenzene under a nitrogen atmosphere was cooled to 2° C. Aluminum trichloride (14.45 g, 2.0 eq.) was added over 30 min. such that the temperature was maintained below 5° C. The mixture was then warmed to 25 ° C. with stirring, and the progress of the reaction was monitored by HPLC (area% at 290 nm). Bis-resorcinol products, 2-chloro-4,6-bis-(2,4-dihydroxyphenyl)-s-triazine (2, 20%) and 2,4-bis-(2,4-dihydroxyphenyl)-6-(2,4-dimethylphenyl)-5-triazine (3, 7%) were formed. The target monoresorcinol product 2 -(2,4-dihydroxyphenyl)-4,6-bis-(2,4-dimethylphenyl)-s-triazine (4) was also formed, although in low yield (20%).

Example 5

2-(2,4-Dihydroxyphenyl)-4,6-bis-(2,4-dimethylphenyl)-s-triazine (1). Reaction Temperature of 45° C.

Example 3 was repeated, except the reaction was run at 45° C. instead of 35° C. After only 6 hr., the cyanuric chloride was nearly completely consumed, and HPLC analysis (area % at 290 nm) showed 36.5% 2-(2,4-dihydroxyphenyl)-4,6-bis(2,4-dimethylphenyl)-s-triazine (4) and only 3.9 area % bis-resorcinol-triazine products: 2-chloro-4,6-bis-(2,4-dihydroxyphenyl)-5-triazine (2,1.4 area %) and 2,4-bis-(2,4-dihydroxyphenyl)-6-(24-dimethylphenyl)-s-triazine (3, 2.5 area %). After 26 hr. at 45° C., the yield of 1 was increased to 41.8% with 4.8 area % of 2,4-bis-(2,4-dihydroxyphenyl)-6-(2,4-dimethylpheny)-s-triazine (3).

These experiments taken together demonstrate that the yield of 2-(2,4-dihydroxy-phenyl)-4,6-bis(2,4-dimethylphenyl)-s-triazine (4) can be optimized and the yield of bis-resorcinol-s-triazine products can be minimized using the appropriate amount of aluminum chloride and temperature. Any further improvements in yield obtained by optimization of these variables is considered within the scope of this invention

Example 6

2-(2,4-Dihydroxyphenyl)-4,6-bis(2,4-dimethylphenyl)-s-triazine (1). Use of Ortho-dichlorobenzene as the Solvent.

The basic procedure of Example 3 was followed, except ortho-dichlorobenzene was used as the solvent in place of chlorobenzene. A mixture of 1.84 g cyanuric chloride (10 mmol), 2.12 g of m-xylene (2 eq.), and 1.10 g of resorcinol (1 eq.) in 20 mL o-dichlorobenzene under a nitrogen atmosphere was cooled to 4° C. Aluminum trichloride (3.00 g) was added over 20 mm. such that the temperature was maintained below 6° C. The mixture was then warmed to 35° C. with stirring, and the progress of the reaction was monitored by HPLC. After 17.5 hr. at 35° C., HPLC analysis (area % at 290 nm) showed 37.1% 2-(2,4-dihydroxyphenyl)-4,6-bis(2,4-dimethylphenyl)-5-triazine (4) with 9.0% bis-resorcinol-triazine products: 2-chloro-4,6-bis-(2,4-dihydroxyphenyl)-s-triazine (2, 3.0%) and 2,4-bis-(2,4-dihydroxyphenyl)-6-(2,4-dimethylphenyl)-s-triazine (3, 6.0%).

This experiment demonstrates that 2-(2,4-dihydroxyphenyl)-4,6-bis(2,4-dimethylphenyl)-s-triazine can be prepared and the yield of bis-resorcinol-s-triazine products can be minimized using solvents other than chlorobenzene. The use of solvents other than chlorobenzene for this process is therefore considered within the scope of this invention.

Example 7

2-(2,4-Dihydroxyphenyl)-4,6-bis(3,4-dimethylphenyl)-5-triazine (5) and 2-(2,4-Dihydroxyphenyl)-4,6-bis(2,3-dimethylphenyl)-s-triazine (6)

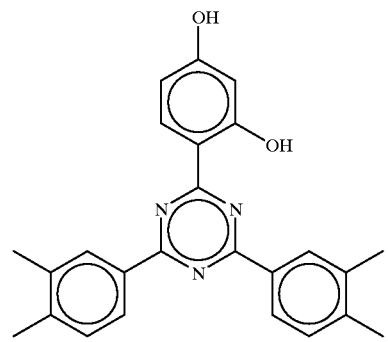

5

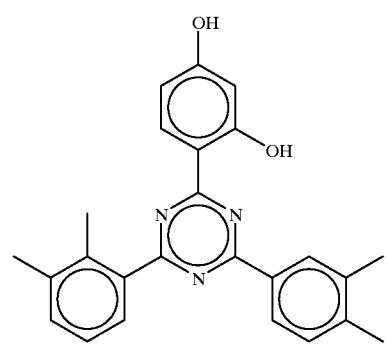

6

The basic procedure of Example 5 was followed, except 2 eq. of ortho-xylene was used as the aromatic reactant in place of 2 eq. of meta-xylene, and chlorobenzene was use as the solvent. The progress of the reaction was monitored by HPLC. After 18 hr. at 35° C., HPLC analysis (area % at 290 nm) showed 35.7% bis-(ortho-xylyl)-mono-resorcinol-s-triazines 34.0% 2-(2,4-dihydroxyphenyl)-4,6-bis(3,4-dimethylphenyl)-s-triazine (5) and 1.7% 2-(2,4-dihydroxyphenyl-4-(3,4-dimethylphenyl)-6-(2,3-dimethylphenyl)-s-triazine (6); with 3.8% 2- chloro-4,6-bis-(2,4-dihydroxyphenyl)-5-triazine and 3.6% 2,4-bis(2,4-dihydroxyphenyl)-6-(3,4-dimethylphenyl)-s-triazine.

Example 8

2-(2,4-Dihydroxyphenyl)-4,6-bis(4-methylphenyl)-5-triazine (7)

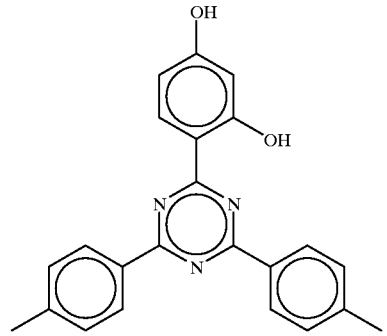

The basic procedure of Example 7 was followed, except 2 eq. of toluene was used as the aromatic reactant in place of 2 eq. of meta-xylene. The progress of the reaction was monitored by HPLC (peak detection at 290 nm). After 23 hr. at 35° C., HPLC analysis showed the formation of 17.3% 2-(2,4-dihydroxyphenyl)-4,6-bis(4-methylphenyl)s-triazine (7).

What is claimed is:

1. A process for preparing a composition comprising one or more triazine compounds of Formula A:

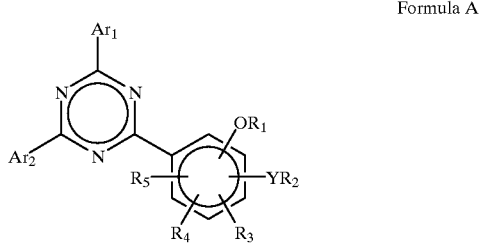

wherein $R_1$ is hydrogen, $R_2$ is hydrogen, alkyl of 1 to 24 carbon atoms, alkenyl of 2 to 24 carbon atoms, acyl of 1 to 24 carbon atoms, aryl of 6 to 24 carbon atoms, cycloalkyl of 5 to 24 carbon atoms, cycloacyl of 5 to 24 carbon atoms, aralkyl of 7 to 24 carbon atoms, aracyl of 6 to 24 carbon atoms and, when Y is a direct bond, halogen, $R_3$, $R_4$ and $R_5$ are the same or different and each is hydrogen, halogen, alkyl of 1 to 24 carbon atoms, alkenyl of 2 to 24 carbon atoms, acyl of 1 to 24 carbon atoms, aryl of 6 to 24 carbon atoms, cycloalkyl of 5 to 24 carbon atoms, cycloacyl of 5 to 24 carbon atoms, aralkyl of 7 to 24 carbon atoms, aracyl of 6 to 24 carbon atoms, OR, NRR', CONRR', OCOR, CN, SR, $SO_2R$, $SO_3H$, $SO_3M$, wherein M is an alkali metal, R and R' are the same or different and each is hydrogen, alkyl of 1 to 24 carbon atoms, alkenyl of 2 to 24 carbon atoms, acyl of 1 to 24 carbon atoms, aryl of 6 to 24 carbon atoms, cycloalkyl of 5 to 24 carbon atoms, cycloacyl of 5 to 24 carbon atoms, aralkyl of 7 to 24 carbon atoms, or aracyl of 6 to 24 carbon atoms, optionally with either of $R_3$ and $R_4$, or $R_4$ and $R_5$, taken together being a part of a saturated or unsaturated fused carbocyclic ring optionally containing O, N or S atoms in the ring, with the proviso that when $R_3$, $R_4$ or $R_5$ is NRR', R and R' are not both hydrogen, and Y is a direct bond, O, NR", or SR", wherein R" is hydrogen, alkyl of 1 to 24 carbon atoms, alkenyl of 2 to 24 carbon atoms, acyl of 1 to 24 carbon atoms, aryl of 6 to 24 carbon atoms, cycloalkyl of 5 to 24 carbon atoms, cycloacyl of 5 to 24 carbon atoms, aralkyl of 7 to 24 carbon atoms or aracyl of 6 to 24 carbon atoms; and $Ar_1$ and $Ar_2$ are the same or different, and each independently is a radical of a compound of Formula B:

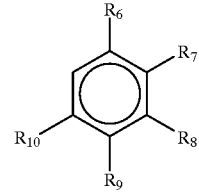

Formula B wherein $R_6$, $R_7$, $R_8$, $R_9$ and $R_{10}$ are the same or different and each is hydrogen, halogen, alkyl of 1 to 24 carbon atoms, aryl of 6 to 24 carbon atoms, alkenyl of 2 to 24 carbon atoms, acyl of 1 to 24 carbon atoms, aralkyl of 7 to 24 carbon atoms, aracyl of 6 to 24 carbon atoms, NRR', CONRR', CN, SR, $SO_2R$, $SO_3H$, $SO_3M$, wherein M is an alkali metal, R and R' are as defined above, and R'" is alkyl of 1 to 24 carbon atoms, aryl of 6 to 24 carbon atoms, alkenyl of 2 to 24 carbon atoms, acyl of 1 to 24 carbon atoms, cycloalkyl of 5 to 24 carbon atoms, cycloacyl of 5 to 24 carbon atoms, aralkyl of 7 to 24 carbon atoms, or aracyl of 6 to 24 carbon atoms, and optionally with either of $R_6$ and $R_7$ taken together, $R_7$ and $R_8$ taken together, $R_8$ and $R_9$ taken together, or $R_9$ and $R_{10}$ taken together being a part of a saturated or unsaturated fused carbocyclic ring optionally containing O, N or S atoms in the ring, which process comprises a single step of:

simultaneously reacting in the presence of a catalyst, sufficient amounts of a compound of Formula C:

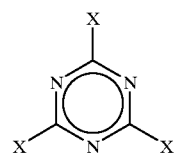

Formula C wherein X is a halogen, a compound of Formula D:

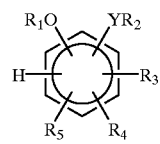

Formula D wherein Y, $R_1$, $R_2$, $R_3$, $R_4$ and $R_5$ are as described above, and a compound of Formula E:

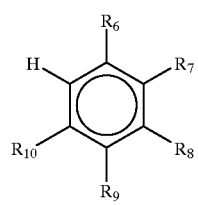

Formula E wherein $R_6$, $R_7$, $R_8$, $R_9$ and $R_{10}$ are as described above,
at a suitable temperature and pressure, and for a time sufficient to produce a reaction mixture comprising the composition.

2. The process of claim 1, wherein $Ar_1$ and $Ar_2$ are the same.

3. The process of claim 1, wherein the catalyst is a Lewis acid and X is chlorine.

4. The process of claim 3, wherein the catalyst is selected from the group consisting of aluminum tribromide, zinc chloride, boron trichloride, titanium tetrachloride, aluminum trichloride, and a mixture thereof.

5. The process of claim 3, wherein the amount of catalyst is from about 1.5 to about 4 equivalents based upon the amount of the compound of Formula C.

6. The process of claim 5, wherein the amount of catalyst is from about 2 to about 3.5 equivalents based upon the amount of the compound of Formula C.

7. The process of claim 6, wherein the amount of catalyst is from about 2.25 to about 2.75 equivalents based upon the amount of the compound of Formula C.

8. The process of claim 1, wherein the amount of the compound of Formula B is from about 1.9 to about 2.5 equivalents based upon the amount of the compound of Formula C.

9. The process of claim 1, wherein the amount of the compound of Formula D is from about 0.5 to about 1.5 equivalents based upon the amount of the compound of Formula C.

10. The process of claim 9, wherein the amount of the compound of Formula D is from about 0.9 to about 1.1 equivalents based upon the amount of the compound of Formula C.

11. The process of claim 1, wherein the reaction occurs at a temperature of between 0° C. and about 120° C.

12. The process of claim 11, wherein the reaction is conducted at a temperature of between about 0° C. and about 90° C.

13. The process of claim 11, wherein the reaction is conducted at a temperature of between about 10° C. and about 60° C.

14. The process of claim 1, wherein the reaction is conducted in a solvent selected from the group selected from the group consisting of aliphatic hydrocarbons, halogenated aliphatic and aromatic compounds, aliphatic and aromatic nitro compounds and carbon disulfide.

15. The process of claim 14, wherein the reaction is conducted in a halogenated solvent.

16. The process of claim 14, wherein the halogenated solvent is selected from the group consisting of chlorobenzene, dichlorobenzene, 1,1,2,2-tetrachlorethane, and mixtures thereof.

17. The process of claim 1, wherein the compounds are reacted for a time from about 2 to about 24 hours.

* * * * *